United States Patent [19]

Downs

[11] 4,115,473

[45] Sep. 19, 1978

[54] POLYOL INTERMEDIATE, POLYESTERS MADE THEREFROM, AND POLYESTER COATING COMPOSITIONS

[75] Inventor: John D. Downs, Bradley, Ill.

[73] Assignee: Mobil Oil Corporation, New York, N.Y.

[21] Appl. No.: 769,249

[22] Filed: Feb. 16, 1977

Related U.S. Application Data

[63] Continuation-in-part of Ser. No. 632,757, Nov. 17, 1975, abandoned.

[51] Int. Cl.$^2$ ............................................. C08L 67/02
[52] U.S. Cl. ............................... 260/850; 260/29.4 R; 260/856; 260/40 R
[58] Field of Search .................. 260/850, 856, 29.4 R, 260/75 R, 40 R

[56] References Cited

U.S. PATENT DOCUMENTS

| Re. 27,279 | 1/1972 | Layman | 260/22 D |
|---|---|---|---|
| 3,449,467 | 6/1969 | Wynstra | 260/850 |
| 3,549,577 | 12/1970 | Stromberg | 260/29.4 R |
| 3,842,021 | 10/1974 | Grant et al. | 260/850 X |
| 3,862,072 | 1/1975 | Sekmakas | 260/29.4 R |
| 3,908,050 | 9/1975 | Gor | 260/850 X |
| 3,954,899 | 5/1976 | Chang et al. | 260/856 X |
| 3,957,709 | 5/1976 | Holzrichter et al. | 260/29.4 R |

*Primary Examiner*—Lucille M. Phynes
*Attorney, Agent, or Firm*—Charles A. Huggett; Hastings S. Trigg

[57] ABSTRACT

There is provided a polyol intermediate that is the reaction product of neopentyl glycol with dimethyl glutarate in a 2:1 molar ratio. This reaction product is polyesterified with a phthalic acid reactant and neopentyl glycol to form a polyester resin. The resultant resin is admixed with an aminoplast and reduced to about 60–75 weight percent solids content with an aromatic hydrocarbon or a mixture of aromatic hydrocarbons to produce a thermosetting coating composition for metal substrates. Films made from this coating composition are hard and tough. They have excellent fabrication characteristics, high reverse impact resistance and excellent flexibility properties and solvent resistance.

5 Claims, No Drawings

POLYOL INTERMEDIATE, POLYESTERS MADE THEREFROM, AND POLYESTER COATING COMPOSITIONS

CROSS-REFERENCE TO RELATED APPLICATIONS

This application is a continuation-in-part of copending application Ser. No. 632,757, filed Nov. 17, 1975 now abandoned.

BACKGROUND OF THE INVENTION

1. Field of the Invention

This invention is directed to novel polyols, polyester resins made therefrom, and thermosetting coating compositions containing such polyester resins and an aminoplast.

2. Description of the Prior Art

In U.S. Pat. No. Re. 27,279, there is disclosed a polyester (alkyd) of a polyol, a phthalic acid, and a dimer fatty acid. Insofar as is now known, the polyol intermediate of this invention has not been proposed. It has been found that polyester coatings made using this polyol intermediate have excellent properties including toughness, flexibility, and impact resistance.

SUMMARY OF THE INVENTION

This invention provides a polyol intermediate that is the reaction product of neopentyl glycol with dimethyl glutarate in a molar ratio of 2 moles neopentyl glycol per mole dimethyl glutarate and at a temperature of between about 120° C. and about 210° C., until at least about 90 weight percent of theoretical methanol of reaction has been removed.

It also provides a polyester resin consisting essentially of, by weight of the total solids charged 35-40 percent of the aforedescribed polyol intermediate, 15-23 percent neopentyl glycol, and 40-45 percent phthalic acid reactant.

It further provides a coating composition comprising the aforedefined polyester resin and an aminoplast, using a weight ratio of polyester/aminoplast of about 90/10 to about 70/30, dissolved in an aromatic hydrocarbon solvent to a total solids content of between about 60 and about 75 weight percent.

DESCRIPTION OF SPECIFIC EMBODIMENTS

An important component of the polyester resins of this invention is a novel polyol intermediate. This is the reaction product obtained by reacting neopentyl glycol with dimethyl glutarate in a ratio of 2 moles neopentyl glycol per mole of dimethyl glutarate. The reaction is essentially an alcoholysis reaction and is carried out at temperatures of between about 120° C. and about 210° C., with the evolution of methanol. The reaction time will usually be between about 2 hours and about 4 hours or until at least about 90 percent of the theoretical methanol has evolved. A catalyst, such as dibutyltin oxide, is generally used in amounts of about 0.05–0.3 weight percent of the reactants.

EXAMPLE 1

Into a reactor provided with a condenser and a receiving vessel, were charged 2 moles neopentyl glycol, 1 mole dimethyl glutarate, and 0.1 weight percent, based on the weight of the reactants, dibutyltin oxide. The reaction mixture was heated to 140° C. under an inert gas (nitrogen) blanket and methanol started to evolve and was collected in the receiver. The temperature was increased to about 200° C. over a period of about 3 hours. Methanol was continuously collected as it evolved and the reaction was continued until about 90 percent of the theoretical methanol had been collected.

Theoretically, the product of Example 1 would have the structure:

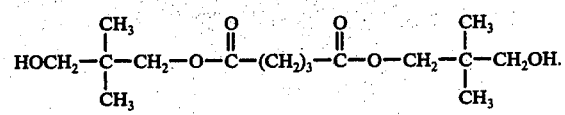

As described hereinafter, however, analysis has indicated that the product is a mixture of various components. It is possible that one component could be a simple 1:1 molar reaction product having the structure:

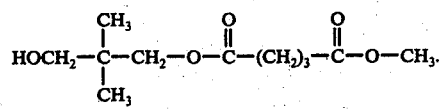

It is also possible that some polycondensation could occur to give components having the general structure:

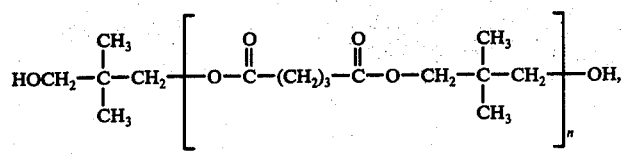

wherein $n$ is a small whole number from 2 to 6.

EXAMPLE 2

Gel permeation chromatography (GPC) was employed with 4' × ⅛" columns having pore sizes of 60Å, 60Å, 200Å, 200Å, to separate the components of the reaction product of Example 1. Neopentyl glycol was identified as a component by comparison with an authentic sample. High resolution gel permeation chromotography was then employed using three 100Å, and two 500Å, columns, each 25 cm. × 7.6 mm. i.d. The three peaks of highest molecular weight components (the first three eluted) were recycled to improve resolution. A dual detector system was used consisting of 254 nm. (nonameter = one billionth of a meter) ultraviolet and a refractometer. Nuclear Magnetic Resonance spectra (each sample dissolved in deuterochloroform) showed differences in structure of the components, particularly with regard to branching and hydroxyl content. A summary of the comparison of the components of the reaction product of Example 1 is set forth in Table 1.

TABLE I

| Component (highest to lowest molecular weight) | Area % of Peak (GPC) | Identification |
|---|---|---|
| 1 | 35% | Ester with branching and hydroxyl groups |
| 2 |  | Ester, less branching compared with peak #1 and less hydroxyl content |
| 3 |  | Ester, considerably higher hydroxyl content compared with peaks #1 and #2 |
| 4 | 26% | Ester, similar to peak #3 but lower molecular weight |
| 5 | 28% | Ester, similar to peak #4 but lower molecular weight |
| 6 | 0.7% | Ester, lower molecular weight |
| 7 | 11% | Neopentyl glycol |

The hydroxyl value of 371 and the number average molecular weight of 311 of the reaction product of Example 1 conform to the theoretical values expected for a simple diester with hydroxyl end groups, i.e., the theoretical product. The data in Table I, however, indicate a mixture of components having variations in structure and molecular weight. Accordingly, it will be appreciated that any designation assigned to this reaction product, other than a definition comprising a recitation of the process of producing it, is not accurately descriptive of it.

The polyester resin of this invention is prepared by precondensation of polyol intermediate (Example 1) neopentyl glycol, and a phthalic acid reactant.

The phthalic acid reactant can be phthalic acid or anhydride, isophthalic acid, terephthalic acid and derivatives thereof, such as hexachlorophthalic acid or anhydride, or endomethylene tetrahydrophthalic acid or anhydride. Isophthalic acid, either alone or in admixture with lesser amounts of other phthalic acids is preferred.

The polycondensation reaction is carried out using, based upon the total weight of charge, 35-40 percent polyol intermediate, 15-23 percent neopentyl glycol and 40-45 percent phthalic acid reactant. Preferably, a catalyst, such as dibutyltin oxide, is used. The polycondensation reaction is carried out at temperatures of 225°-250° C. for a period of time of 6-8 hours. The reaction is complete when the Acid Number is between about one and about 20. Near the end of the reaction when in the order of 90 percent of the water of reaction has been collected, removal of the remainder of the water can be facilitated by adding 2-4 weight percent of an azeotroping agent, such as toluene or xylene.

EXAMPLE 3

A mixture of 37.3 parts by weight of the polyol intermediate (reaction product of Example 1), 20.1 parts by weight of neopentyl glycol, 13.1 parts by weight of phthalic anhydride, and 29.4 parts by weight of isophthalic acid was charged to a reactor equipped with a condenser and receiving vessel. The mixture was heated to 240°-250° C. in 3-4 hours and water of reaction was removed and collected as it formed. When about 90 percent of the water of reaction had been collected, 2 parts by weight of toluene was added and the reaction was continued, using azeotropic distillation to remove water and collecting water and returning toluene to the reactor. When the Acid Number reached a value of 1 (maximum), the product was diluted to 60 weight percent solids with commercial mixture of aromatic hydrocarbon solvents having a boiling range of 370°-510° F. (187.8°-265.6° C.).

It has been found that the reaction to prepare the polyol intermediate reaction product (Example 1) can be carried out in the presence of excess neopentyl glycol. Accordingly, in practice, it is preferred to carry out the preparation of the polyol intermediate and the polycondensation to polyester resin (Examples 1 and 3) sequentially in the same reactor. Thus, the preparation of the polyol intermediate can be carried out using all the neopentyl glycol required to make both the polyol intermediate and the polyester resin. Subsequently, the phthalic acid reactant is added and the polycondensation is carried out. This is demonstrated in the following example.

EXAMPLE 4

Into a reactor equipped with a condenser and receiving vessel, were charged 267.35 lbs. of neopentyl glycol, 114.7 lbs. of dimethyl glutarate, and 0.38 lb. of dibutyltin oxide. The reactants were heated to 140° C. under a nitrogen gas blanket and methanol commenced to evolve. It was continuously collected over a 2-3 hour period while the temperature was increased to 200° C., until 90 percent of the theoretical methanol (45.53 lbs.) had been collected.

Then, there were charged 77.08 lbs. phthalic anhydride, 172.56 lbs. isophthalic acid and 0.25 lb. dibutyltin oxide. The reactants were heated to 240°-250° C. in 3-4 hours and water of reaction was collected. About 1 hour after a temperature of about 240° C. had been reached, 90 percent of the water had been collected. The condenser was converted to azeotropic distillation using a trap to separate and remove water and to return the azeotroping agent to the reactor. Toluene (14.4 lbs.) was added and azeotropic distillation was carried out until the Acid Number of the reaction mixture was 1 or less. The total water collected was 46.79 lbs. The resulting polyester resin was diluted to 60 weight percent solids with 345.6 lbs. of a commercial mixture of aromatic hydrocarbon solvents having a boiling range of 370°-510° F. (187.8°-265.6° C.), forming a polyester resin solution for use in a coating formulation.

EXAMPLE 5

Into a reactor equipped with a condenser and receiving vessel, were charged 251.17 lbs. of neopentyl glycol, 121.66 lbs. of dimethyl glutarate, and 0.38 lb. of dibutyltin oxide. The reactants were heated to 140° C. under a nitrogen gas blanket and methanol commenced to evolve. It was continuously collected over a 2-3 hour period while the temperature was increased to 200° C., until 90 percent of the theoretical methanol (48.51 lbs.) had been collected.

Then, there were charged 81.77 lbs. phthalic anhydride, 183.06 lbs. isophthalic acid and 0.26 lb. dibutyltin oxide. The reactants were heated to 240°-250° C. in 3-4 hours and water of reaction was collected. About 1 hour after a temperature of about 240° C. had been reached, 90 percent of the water had been collected. The condenser was converted to azeotropic distillation using a trap to separate and remove water and to return the azeotroping agent to the reactor. Toluene (14.4 lbs.) was added and azeotropic distillation was carried out until the Acid Number of the reaction mixture was 14-18. The total water collected was 49.79 lbs. The resulting polyester resin was diluted to 60 weight percent solids with 345.6 lbs. of a commercial mixture of aromatic hydrocarbon solvents having a boiling range of 370°–510° F. (187.8°–165.6° C.), forming a polyester resin solution for use in coating formulation.

COATING COMPOSITIONS

The polyester resin can be thermoset using a conventional aminoplast cross-linking agent. Such agents are well known in the art. There can be used any of the thermosetting alkylated aminoplast resins, such as the urea-aldehyde resins, the melamine-aldehyde resins, the dicyandiamide-aldehyde resins and other aminoplast-aldehyde resins such as those triazine resins produced by the reaction of an aldehyde with formoguanamine, ammeline, 2-chloro-4, 6-diamino-1,3,5-triazine, 2-phenyl-p-oxy-4, 6-diamino-1,3,5-triazine, 6-methyl-2,4-diamino-1,3,5-triazine; 2,4,6-trihydrazine-1,3,5-triazine, and 2,4,6-triethyl-triamino-1,3,5-triazine. As aldehydes used to react with the amino compound to form the resinous material, one may use such aldehydes as formaldehyde, acetaldehyde, crotonic aldehyde, acrolein, or compounds which engender aldehydes, such as hexamethylenetetramine, paraldehyde, paraformaldehyde, and the like.

A preferred class of aminoplasts is a melamine-formaldehyde resin that has been alkylated with methanol, butanol, or a mixture of methanol and butanol. Typical of this class is hexamethoxymethyl melamine. In general, a solvent such as butanol or ethoxyethyl acetate may be used.

Although not essential, it is preferable to use an acid cross-linking catalyst, such as p-toluenesulfonic acid. Other suitable catalysts include acid phosphates, such as methyl acid phosphate and butyl acid phosphate; acid pyrophosphates, such as dimethyl acid pyrophosphates; organic acid sulfate esters; and other organic sulfonic acids.

Although a pigment is not necessary, it is preferred to incorporate a pigment into the coating composition of this invention. The preferred pigment is titanium dioxide for white coats, but any well known filler pigment can be used, such as zinc oxide, bentonite, talc, silica, ochers, and chrome yellows or greens.

Other well known adjuvants may be added, such as flow control agents and waxes. A preferred flow control agent is sodium dioctyl sulfosuccinate, but others utilizable include sodium dihexyl sulfosuccinate, sodium diamyl sulfosuccinate, isopropyl naphthalene sulfosuccinate, and sorbitan monolaurate, monopalmitate, or monooleate. Waxes, if used, are added as slurries or emulsions of petroleum (paraffin) wax, natural waxes such as montan wax, beeswax, and carnauba wax, or synthetic waxes such as polyethylene wax.

To prepare the final coating composition the polyester resin solution is admixed with the aminoplast mixture. These components will usually be blended using between about 70 and about 90 parts by weight of polyester resin solution to between about 30 and about 10 parts by weight aminoplast mixture. Other ratios can be used, bearing in mind, however, that higher aminoplast concentrations tend to increase brittleness of the final baked finish and that lower aminoplast concentrations tend to increase back temperature or bake time, or both. The final product should have a solids content of between about 60 and about 75 wt.%.

These coating compositions can be applied to the desired substrate as such or, in some cases, they may be diluted ethoxyethyl acetate or aromatic solvent or a 50/50 mixture thereof. After application the coating is baked for about 3 seconds to about 5 minutes at between about 250° F. and about 600° F. A preferred bake is for about 40 seconds at 560° F.

Suitable substrates are paper, metallic foil and can stock metals (approximately 10 mil stock). The coating can be applied by roll coat, flow coat or gravure coat.

EXAMPLE 6

The polyester resin solution (Example 4) was mixed with hexamethoxymethylmelamine aminoplast to provide a solution containing 85/15 weight ratio polyester-/aminoplast on a non-volatile basis. The product was pigmented with $TiO_2$ at about 0.85/1.00 pigment/binder weight ratio. About 0.5 weight percent p-toluene sulfonic acid was added as a catalyst.

The resultant coating composition was applied to 26 gauge hot dip galvanized steel panels and cured for about 40 seconds at 560° F. After cooling, the panels were subjected to various tests with the results set forth in Table II.

TABLE II

| | |
|---|---|
| Flexibility, Olsen | #8 |
| Wedge-bend Flexibility | No tape pull-off |
| Fabrication 180° Bend | OT - No flake (10) |
| Impact Resistance | 80" lbs. - reverse |
| Pencil Hardness | H-2H |
| Solvent Resistance (MEK rubs) | 50 MEK double rubs |

Impact resistance was determined in accordance with ASTM Designation D2794-69. The other test procedures were as follows:

Flexibility, Olsen — A Tinius Olsen Testing Machine equipped with a 1 inch diameter forming die and a ⅝ inch diameter ball is used. The test panel is clamped between the ball and the die and load is applied to fracture the metal. Scotch brand tape is applied to the formed cup and removed quickly. The adhesion rating is made by comparison with eight standard rating photographs, wherein #1 is the poorest rating and #8 is the best.

Wedge-bend flexibility — The panels are bent into a U-shape and placed under the hinge of the tester which slopes downward from ⅛" to 0" and pressed. This results in a wedge-bend sloping from 0" to ⅛" over a distance of 100 mm. Scotch tape is then applied to the wedge and removed quickly. Cracking or removal of the film is measured in millimeters along the bend from 0" toward the ⅛" and recorded as percent failure.

Fabrication 180° Bend (OT Bend) — The panel is manually bent into a U-shape. A number of thicknesses of the substrate (in this case, no thicknesses or OT) are placed in the bend area and the entire assembly is placed in the jaws of a press and pressed. Scotch tape is applied across the bend and removed quickly. The adhesion of the coating after bending is rated on a scale of 0 to 10 with 10 representing perfect, i.e., no coating was pulled off with the tape.

Pencil hardness test — A set of pencils ranging from 6B (soft) to 6H (hard) are used, starting with the hard end of the set. These pencils are pushed in turn into the film. The first pencil which crumbles instead of penetrates indicates the pencil hardness.

MEK Double Rubs — A pad of felt (2" square) soaked in MEK (methylethyl ketone) is rubbed back and forth across the coated surface, while the panel is resting on a firm surface. Each stroke is 2½–3" in length at a uniform pressure of about 900 grams and at a rate of about 100 rubs per minute. The pad is re-soaked with MEK after 50 double rubs, or before, if increase in friction makes it necessary. One double rub is considered as one back and forth stroke. Fifty double rubs should only slightly dull the surface in the center area of the rub.

EXAMPLE 7

Following the blending procedure of Example 6, a pigmented coating composition was made using the polyester resin solution of Example 5. This composition was applied to electrocoated tin plated steel and cured for about 41 seconds at 560° F. Test results are set forth in Table III.

TABLE III

| | |
|---|---|
| Flexibility, Olsen | #8 |
| Fabrication 180° Bend | OT - No flake (10) |
| Pencil Hardness | H |
| Solvent Resistance (MEK rubs) | 60+ |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A coating composition comprising the polyester resin which consists essentially of, by weight of the total solids charged, 35–40 percent of a polyol intermediate that is the reaction product of neopentyl glycol with dimethyl glutarate in a molar ratio of 2 moles neopentyl glycol per mole dimethyl glutarate and at a temperature of between about 120° C. and about 210° C., until at least about 90 weight percent of theoretical methanol of reaction has been removed, 15–23 percent neopentyl glycol, and 40–45 percent phthalic acid reactant; said resin having an Acid Number between about 1 and about 20, and an aminoplast, using a weight ratio of polyester/aminoplast of about 90/10 to about 70/30, dissolved in an aromatic hydrocarbon solvent to a total solids content of between about 60 and about 75 weight percent.

2. The coating composition of claim 1, wherein said phthalic acid reactant is a mixture of phthalic anhydride and isophthalic acid and said aminoplast is hexamethoxymethylmelamine.

3. The coating composition of claim 1 containing a pigment.

4. The coating composition of claim 3, wherein the pigment is $TiO_2$ in a pigment/binder ratio of about 0.85/1.

5. The coating composition of claim 2 containing $TiO_2$ pigment in a pigment/binder ratio of about 0.85/1.

* * * * *